US00PP35946P2

(12) United States Plant Patent
Miyazaki

(10) Patent No.: US PP35,946 P2
(45) Date of Patent: Jul. 2, 2024

(54) ***PETUNIA* PLANT NAMED 'SURF IKUSIRO'**

(50) Latin Name: ***Petunia* x *hybrida***
Varietal Denomination: Surf Ikusiro

(71) Applicant: Kiyoshi Miyazaki, Shiga (JP)

(72) Inventor: Kiyoshi Miyazaki, Shiga (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 18/126,276

(22) Filed: Mar. 24, 2023

(51) Int. Cl.
*A01H 5/02* (2018.01)
*A01H 6/82* (2018.01)

(52) U.S. Cl.
USPC ..... Plt./356.23

(58) Field of Classification Search
USPC ..... Plt./356.23
CPC . A01H 5/02; A01H 5/00; A01H 6/824; A01H 6/82
See application file for complete search history.

(56) References Cited

PUBLICATIONS

BFG Supply Co. Spring Trials 2022 Report, retrieved on Jul. 20, 2023 online at https://www.bfgsupply.com/media/6231/2022-spring-trials-report-final.pdf, cover page, one introductory page, pp. 5-6 and two back cover pages. (Year: 2022).*

Suntory Flowers 2023 Catalog, retrieved on Jul. 20, 2023 online at https://suntoryflowers.com/wp-content/uploads/2022/03/2023-SuntoryCatalog.pdf, pp. 1-3, 6. (Year: 2023).*

* cited by examiner

*Primary Examiner* — June Hwu
(74) *Attorney, Agent, or Firm* — C. Anne Whealy

(57) ABSTRACT

A new and distinct cultivar of *Petunia* plant named 'Surf Ikusiro', characterized by its upright to outwardly spreading plant habit; vigorous growth habit; freely branching habit; freely flowering habit; long flowering period; large flowers that are light red in color with conspicuous darker red-colored venation; and good garden performance.

1 Drawing Sheet

Figure 1:
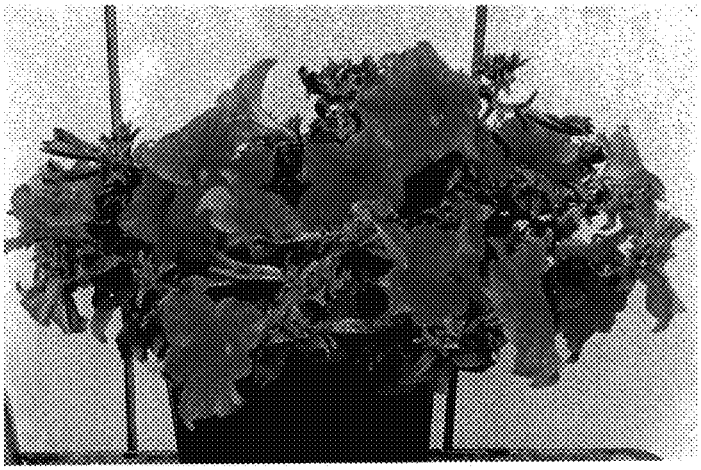

Botanical designation: *Petunia* x *hybrida*.
Cultivar denomination: 'SURF IKUSIRO'.

BACKGROUND OF THE INVENTION

The present invention relates to a new and distinct cultivar of *Petunia* plant, botanically known as *Petunia* x *hybrida* and hereinafter referred to by the name 'Surf Ikusiro'.

The new *Petunia* plant is a product of a planned breeding program conducted by the Inventor in Higashiomi, Shiga, Japan. The objective of the breeding program is to create new upright to spreading and freely-branching habit *Petunia* plants with numerous large attractive flowers.

The new *Petunia* plant originated from a cross-pollination made by the Inventor in June, 2016 in Higashiomi, Shiga, Japan of a proprietary selection of *Petunia* x *hybrida* identified as code designation Px8284-4, not patented, as the female, or seed, parent with a proprietary selection of *Petunia* x *hybrida* identified as code designation SF-Rs, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in June, 2017.

Asexual reproduction of the new *Petunia* plant by terminal vegetative cuttings in a controlled greenhouse environment in Higashiomi, Shiga, Japan since April, 2018 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Surf Ikusiro'. These characteristics in combination distinguish 'Surf Ikusiro' as a new and distinct *Petunia* plant:

1. Upright to outwardly spreading plant habit.
2. Vigorous growth habit.
3. Freely branching habit.
4. Freely flowering habit.
5. Long flowering period.
6. Large flowers that are light red in color with conspicuous darker red-colored venation.
7. Good garden performance.

Plants of the new *Petunia* can be compared to plants of the female parent selection. Plants of the new *Petunia* differ primarily from plants of the female parent selection in flower color as flowers of plants of the new *Petunia* are light red in color whereas flowers of plants of the female parent selection are white in color. In addition, plants of the new *Petunia* are more mounding than and not as compact as plants of the female parent selection.

Plants of the new *Petunia* can be compared to plants of the male parent selection. Plants of the new *Petunia* differ primarily from plants of the male parent selection in flower color as flowers of plants of the new *Petunia* are light red in color whereas flowers of plants of the male parent selection are rose in color. In addition, plants of the new *Petunia* are more mounding than and not as trailing as plants of the male parent selection.

Plants of the new *Petunia* can also be compared to plants of the *Petunia* x *hybrida* 'Surf Ikuyoko', disclosed in U.S. Plant Pat. No. 34,985. In side-by-side comparisons, plants of the new *Petunia* and 'Surf Ikuyoko' differ primarily in the following characteristics:

1. Plants of the new *Petunia* have longer internodes and fewer leaves per lateral branch than plants of 'Surf Ikuyoko'.
2. Plants of the new *Petunia* have slightly smaller flowers than plants of 'Surf Ikuyoko'.
3. Plants of the new *Petunia* and 'Surf Ikuyoko' differ in flower color as flowers of plants of the new *Petunia* are light red in color whereas flowers of plants of 'Surf Ikuyoko' are bright reddish purple in color.
4. Petal venation of plants of the new *Petunia* is more distinct and conspicuous than petal venation of plants of 'Surf Ikuyoko'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet (FIG. 1) is a side perspective view of a typical flowering plant of 'Surf Ikusiro' grown in a container.

Figure 2:
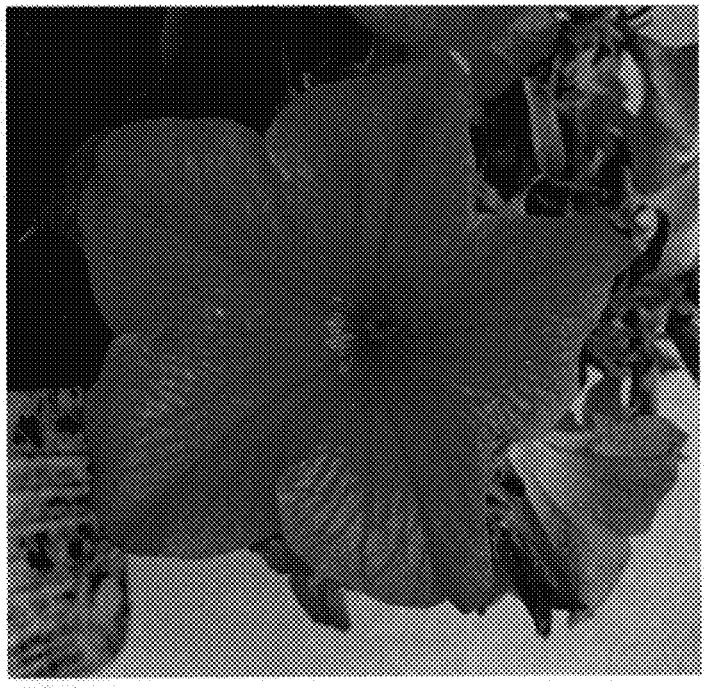

The photograph at the bottom of the sheet (FIG. 2) is a close-up view of typical flowers of 'Surf Ikusiro'.

DETAILED BOTANICAL DESCRIPTION

The aforementioned photographs and following observations, measurements and values describe plants grown during the late spring and early summer in 24-cm containers in an outdoor nursery in Higashiomi, Shiga, Japan and under cultural practices typical of commercial *Petunia* production. During the production of the plants, day temperatures averaged 23 C and night temperatures averaged 13 C. Plants were six months old when the photographs and description were taken. In the following description, color references are made to The Royal Horticultural Society Colour Chart, 2015 Edition, except where general terms of ordinary dictionary significance are used.

Botanical classification: *Petunia* x *hybrida* 'Surf Ikusiro'.

Parentage:

*Female, or seed, parent*.—Proprietary selection of *Petunia* x *hybrida* identified as code designation Px8284-4, not patented.

*Male, or pollen, parent*.—Proprietary selection of *Petunia* x *hybrida* identified as code designation SF-Rs, not patented.

Propagation:

*Type*.—By terminal vegetative cuttings.

*Time to initiate roots, summer and winter*.—About one week at temperatures about 15 C to 20 C.

*Time to produce a rooted young plant, summer and winter*.—About three weeks at temperatures about 15 C to 20 C.

*Root description*.—Fibrous; typically white in color; actual color of the roots is dependent on substrate composition, water quality, fertilizer type and formulation, substrate temperature and physiological age of roots.

*Rooting habit*.—Freely branching; dense.

Plant description:

*Plant form and growth habit*.—Upright to outwardly spreading plant habit; freely branching habit with numerous lateral branches developing per plant; pinching enhances lateral branch development; vigorous growth habit.

*Plant height*.—About 26 cm.

*Plant diameter*.—About 50 cm.

Lateral branch description:

*Length*.—About 23 cm.

*Diameter*.—About 3.9 mm.

*Internode length*.—About 2.7 cm.

*Strength*.—Strong, flexible.

*Aspect*.—Upright to outwardly.

*Texture*.—Densely pubescent; rough.

*Color*.—Close to 138B.

Leaf description:

*Quantity and arrangement*.—About eleven leaves per lateral branch; alternate, simple.

*Length*.—About 5.7 cm.

*Width*.—About 3.6 cm.

*Shape*.—Elliptic.

*Apex*.—Acute.

*Base*.—Attenuate.

*Margin*.—Entire; undulate.

*Texture, upper and lower surfaces*.—Densely pubescent; rough.

*Venation pattern*.—Pinnate; reticulate.

*Color*.—Developing and fully expanded leaves, upper surface: Close to 138A; venation, close to 138B. Developing and fully expanded leaves, lower surface: Close to 139C; venation, close to 138C.

*Petioles*.—Length: About 3 mm. Diameter: About 3 mm. Texture, upper and lower surfaces: Densely pubescent; rough. Color, upper and lower surfaces: Close to 138B.

Flower description:

*Flower arrangement and habit*.—Large single-type salverform flowers arising from upper leaf axils; freely flowering habit with usually about four flowers developing per lateral branch and about 52 flower buds and flowers developing per plant; flowers face upright to mostly outwardly.

*Fragrance*.—None detected.

*Natural flowering season*.—Early flowering habit; plants of the new *Petunia* initiate and develop flowers about three to four weeks after planting; long flowering period, flowering commences naturally during the spring and plants flower continuously throughout the summer and into the late autumn in Japan.

*Flower longevity*.—Individual flowers last about seven to ten days on the plant; flowers not persistent.

*Flower buds*.—Length: About 5.7 cm. Diameter: About 1.9 cm. Shape: Cylindrical. Color: Immature sepals, close to 197B; immature petals, close to 184B with venation, close to 148A.

*Flower diameter*.—About 8.8 cm.

*Flower height*.—About 5.9 cm.

*Flower tube length*.—About 3.25 cm.

*Flower tube diameter, distally*.—About 1.8 cm.

*Flower tube diameter, proximally*.—About 4.5 mm.

*Corolla*.—Quantity and arrangement: Five in a single whorl, fused at the base and opening into a flared trumpet. Petal length from throat: About 3.4 cm. Petal width: About 4 cm. Petal shape: Roughly spatulate. Petal apex: Cuspidate. Petal margin: Entire; moderately undulate. Petal texture, upper and lower surfaces: Smooth, glabrous; velvety. Throat texture: Smooth, glabrous. Tube texture: Smooth, glabrous. Color: Petal, when opening, upper surface: Close to 50A. Petal, when opening, lower surface: Close to 51B. Petal, fully opened, upper surface: Close to 51A; venation, close to 47B; color becoming closer to 54B with subsequent development. Petal, fully opened, lower surface: Close to 48B; venation, close to 48B; color does not change with subsequent development. Throat: Distally, close to N155C; mid-section, close to 150B; proximally, close to 150C; venation, close to 183C. Tube: Distally and mid-section, close to 146C; proximally, close to 150C; venation, similar to lamina colors.

*Calyx*.—Arrangement: One star-shaped calyx tube with five sepals arranged in a single whorl and fused at the base. Sepal length: About 1.5 cm. Sepal width: About 4.4 mm. Sepal shape: Linear. Sepal apex: Acute. Sepal margin: Entire; undulate. Sepal texture, upper and lower surfaces: Densely pubescent; rough. Color, upper surface: Close to 137A. Color, lower surface: Close to 138A.

*Peduncles*.—Length: About 1.7 cm. Diameter: About 2.2 mm. Strength: Moderately strong, flexible. Aspect: Upright to outwardly. Texture: Densely pubescent; rough. Color: Close to 138B.

*Reproductive organs*.—Stamens: Quantity per flower: Five. Filament length: About 2 cm. Filament color: Close to 145C. Anther shape: Ellipsoidal. Anther size: About 2.6 mm by 2.8 mm. Anther color: Close to 145C. Pollen amount: Moderate. Pollen color: Close to 8C. Pistils: Quantity per flower: One. Pistil length: About 2.5 cm. Style color: Close to 150C. Stigma shape: Transversely ellipsoidal. Stigma color: Close to 150B. Ovary color: Close to 151D. Seeds and fruits: To date, seed and fruit development have not been observed on plants of the new *Petunia*.

Garden performance: Plants of the new *Petunia* have been observed to have good garden performance and to tolerate rain, wind and temperatures ranging from about 5 C to about 35 C.

Pathogen & pest resistance: To date, plants of the new *Petunia* have not been observed to be resistant to pathogens and pests common to *Petunia* plants.

It is claimed:

1. A new and distinct *Petunia* plant named 'Surf Ikusiro' as illustrated and described.

* * * * *